(12) United States Patent
Toronyi et al.

(10) Patent No.: US 11,506,052 B1
(45) Date of Patent: Nov. 22, 2022

(54) FRAMEWORK AND INTERFACE FOR ASSESSING RESERVOIR MANAGEMENT COMPETENCY

(71) Applicant: QRI GROUP, LLC, Houston, TX (US)

(72) Inventors: Robert M. Toronyi, Danville, CA (US); Nansen G. Saleri, Houston, TX (US); Jeremy Brown, Houston, TX (US)

(73) Assignee: QRI GROUP, LLC, Houston, TX (US)

( * ) Notice: Subject to any disclaimer, the term of this patent is extended or adjusted under 35 U.S.C. 154(b) by 737 days.

(21) Appl. No.: 16/448,594

(22) Filed: Jun. 21, 2019

Related U.S. Application Data

(60) Provisional application No. 62/690,187, filed on Jun. 26, 2018.

(51) Int. Cl.
| | |
|---|---|
| *E21B 49/08* | (2006.01) |
| *E21B 47/06* | (2012.01) |
| *G06Q 10/06* | (2012.01) |
| *G01N 33/28* | (2006.01) |
| *E21B 47/047* | (2012.01) |

(52) U.S. Cl.
CPC ........ *E21B 49/0875* (2020.05); *E21B 47/047* (2020.05); *E21B 47/06* (2013.01);
(Continued)

(58) Field of Classification Search
CPC .............. E21B 49/087; E21B 49/0875; E21B 2200/20; E21B 47/047; E21B 47/06;
(Continued)

(56) References Cited

U.S. PATENT DOCUMENTS

| | | |
|---|---|---|
| 3,035,440 A | 5/1962 | Reed |
| 5,984,010 A | 11/1999 | Elias et al. |

(Continued)

FOREIGN PATENT DOCUMENTS

| | | |
|---|---|---|
| CN | 1209860 | 3/1999 |
| CN | 1664575 | 9/2005 |

(Continued)

OTHER PUBLICATIONS

Final Office Action received for U.S. Appl. No. 13/282,315, dated Jun. 25, 2015.

(Continued)

*Primary Examiner* — Nathaniel J Kolb
(74) *Attorney, Agent, or Firm* — Workman Nydegger

(57) ABSTRACT

Embodiments are directed to methods, systems and user interfaces for assessing reservoir management competency for a petroleum producing field. In one scenario, a computer system measures, using various hardware-based sensors positioned in a petroleum reservoir supplying the petroleum producing field, physical or geological characteristics of the petroleum reservoir. The computer system establishes a reservoir management competency scoring system that evaluates a specific set of objective criteria that reflect a level of reservoir management competency at the petroleum producing field, and automatically generates, according to the objective set of criteria of the reservoir management competency scoring system, a reservoir management rating for the petroleum reservoir based at least in part on data measured by the sensors placed in the petroleum reservoir. Then, based on the generated reservoir management rating, the computer system controls operation of production units configured to direct extraction operations at the petroleum producing field.

19 Claims, 7 Drawing Sheets

(52) U.S. Cl.
CPC ..... *G01N 33/2841* (2013.01); *G01N 33/2847* (2013.01); *G06Q 10/06393* (2013.01); *E21B 2200/20* (2020.05)

(58) Field of Classification Search
CPC ............. G06Q 10/063; G06Q 10/0639; G06Q 10/06393; G01N 33/2847; G01N 33/2841
USPC .......................................... 702/6, 11, 12, 13
See application file for complete search history.

(56) References Cited

U.S. PATENT DOCUMENTS

| | | | |
|---|---|---|---|
| 6,101,447 | A | 8/2000 | Poe |
| 6,401,547 | B1 | 6/2002 | Hatfield |
| 7,079,952 | B2 | 7/2006 | Thomas et al. |
| 7,289,942 | B2 | 10/2007 | Yang et al. |
| 7,445,041 | B2 | 11/2008 | O'Brien |
| 7,556,099 | B2 | 7/2009 | Arthur et al. |
| 7,798,219 | B1 | 9/2010 | Harnoy |
| 7,857,047 | B2 | 12/2010 | Remmert et al. |
| 7,890,264 | B2 | 2/2011 | Elphic |
| 7,953,327 | B2 | 5/2011 | Pereira et al. |
| 7,963,327 | B1 | 6/2011 | Saleri et al. |
| 8,145,427 | B1 | 3/2012 | Saleri et al. |
| 8,145,428 | B1 | 3/2012 | Saleri et al. |
| 8,195,401 | B2 | 6/2012 | Ella et al. |
| 8,209,202 | B2 | 6/2012 | Narayanan et al. |
| 8,396,826 | B2 | 3/2013 | Mijares et al. |
| 8,880,422 | B1 | 11/2014 | Lehmann et al. |
| 9,239,961 | B1 | 1/2016 | Cole et al. |
| 9,710,766 | B2 | 7/2017 | Saleri et al. |
| 9,767,421 | B2 | 9/2017 | Saleri et al. |
| 9,792,571 | B1 | 10/2017 | Mandava et al. |
| 9,940,724 | B2 | 4/2018 | Jia et al. |
| 9,946,986 | B1 | 4/2018 | Saleri et al. |
| 10,329,881 | B1 | 6/2019 | Saleri et al. |
| 10,477,157 | B1 | 11/2019 | Shahdi et al. |
| 2001/0015133 | A1 | 8/2001 | Sakai et al. |
| 2001/0037983 | A1 | 11/2001 | Takahashi et al. |
| 2002/0013687 | A1 | 1/2002 | Ortoleva |
| 2002/0120429 | A1 | 8/2002 | Ortoleva |
| 2002/0165671 | A1 | 11/2002 | Middya |
| 2002/0167314 | A1 | 11/2002 | Prammer |
| 2003/0167238 | A1 | 9/2003 | Zeif |
| 2003/0225606 | A1 | 12/2003 | Raghuraman et al. |
| 2004/0015376 | A1 | 1/2004 | Zhu et al. |
| 2004/0153437 | A1 | 8/2004 | Buchan |
| 2004/0158406 | A1 | 8/2004 | Harrison |
| 2004/0220846 | A1 | 11/2004 | Cullick |
| 2005/0038603 | A1 | 2/2005 | Thomas et al. |
| 2005/0149307 | A1 | 7/2005 | Gurpiner et al. |
| 2005/0209912 | A1 | 9/2005 | Venningen et al. |
| 2006/0224369 | A1 | 10/2006 | Yang et al. |
| 2006/0289157 | A1 | 12/2006 | Rao |
| 2007/0016389 | A1 | 1/2007 | Ozgen |
| 2007/0028417 | A1 | 2/2007 | Crichlow |
| 2007/0118346 | A1 | 5/2007 | Wen et al. |
| 2007/0143025 | A1 | 6/2007 | Valdez et al. |
| 2007/0156377 | A1 | 7/2007 | Gurpinar |
| 2007/0017968 | A1 | 8/2007 | Cullick et al. |
| 2007/0179768 | A1 | 8/2007 | Cullick et al. |
| 2007/0183604 | A1 | 8/2007 | Araki et al. |
| 2007/0284107 | A1 | 12/2007 | Crichlow |
| 2008/0052097 | A1 | 2/2008 | Bouzas et al. |
| 2008/0065363 | A1 | 3/2008 | Middya |
| 2008/0091283 | A1 | 4/2008 | Balci et al. |
| 2008/0252898 | A1 | 10/2008 | Pfaff |
| 2008/0262898 | A1 | 10/2008 | Tonchev et al. |
| 2008/0288226 | A1 | 11/2008 | Gurpinar et al. |
| 2009/0005630 | A1 | 1/2009 | Yokoyama et al. |
| 2009/0037115 | A1 | 2/2009 | Magill et al. |
| 2009/0084545 | A1 | 4/2009 | Banerjee et al. |
| 2009/0133871 | A1 | 5/2009 | Skinner et al. |
| 2009/0313772 | A1 | 12/2009 | Talley |
| 2010/0042458 | A1 | 2/2010 | Rashid et al. |
| 2010/0057418 | A1 | 3/2010 | Li et al. |
| 2010/0082142 | A1 | 4/2010 | Usadi et al. |
| 2010/0204972 | A1 | 8/2010 | Hsu et al. |
| 2010/0300682 | A1 | 12/2010 | Thakur et al. |
| 2011/0014088 | A1 | 1/2011 | Zubrin et al. |
| 2011/0054869 | A1 | 3/2011 | Li |
| 2011/0067443 | A1 | 3/2011 | Martinez et al. |
| 2011/0130966 | A1 | 6/2011 | Zhan et al. |
| 2011/0168391 | A1 | 7/2011 | Saleri et al. |
| 2011/0246099 | A1* | 10/2011 | Estrada ............. G01N 33/2847 702/50 |
| 2011/0290479 | A1 | 12/2011 | Izgec |
| 2011/0295656 | A1 | 12/2011 | Venkatasubramanian |
| 2012/0101759 | A1 | 4/2012 | Rai et al. |
| 2012/0232865 | A1 | 9/2012 | Maucec et al. |
| 2012/0292055 | A1 | 11/2012 | Swist |
| 2013/0043025 | A1 | 2/2013 | Scott |
| 2013/0048279 | A1 | 2/2013 | Appel et al. |
| 2013/0110474 | A1 | 5/2013 | Saleri |
| 2013/0110524 | A1 | 5/2013 | Saleri et al. |
| 2013/0110563 | A1 | 5/2013 | Saleri |
| 2013/0110571 | A1 | 5/2013 | Saleri et al. |
| 2013/0151159 | A1 | 6/2013 | Pomerantz et al. |
| 2013/0161502 | A1 | 6/2013 | Pomerantz et al. |
| 2013/0218538 | A1 | 8/2013 | Fuecker et al. |
| 2013/0271757 | A1 | 10/2013 | Kang et al. |
| 2013/0338987 | A1 | 12/2013 | Cheng et al. |
| 2014/0310071 | A1 | 10/2014 | Conradson |
| 2015/0032377 | A1* | 1/2015 | McAuliffe ............ E21B 49/008 702/13 |
| 2015/0040990 | A1 | 2/2015 | Mathiesen et al. |
| 2015/0094994 | A1 | 4/2015 | Sequeira et al. |
| 2015/0269438 | A1 | 9/2015 | Samarasekera et al. |
| 2015/0278407 | A1 | 10/2015 | Vennelakanti et al. |
| 2015/0337631 | A1 | 11/2015 | Matringe et al. |
| 2015/0346010 | A1 | 12/2015 | Matringe et al. |
| 2015/0371345 | A1 | 12/2015 | Jeffers |
| 2016/0214715 | A1 | 7/2016 | Meffert |
| 2016/0369616 | A1 | 12/2016 | Leblanc et al. |
| 2017/0058656 | A1 | 3/2017 | Benson et al. |
| 2017/0335665 | A1 | 11/2017 | Saleri |
| 2017/0364795 | A1* | 12/2017 | Anderson .............. G06N 20/10 |
| 2018/0053055 | A1 | 2/2018 | Finding et al. |
| 2018/0053352 | A1 | 2/2018 | Finding et al. |
| 2018/0075605 | A1 | 3/2018 | Jia et al. |
| 2018/0171788 | A1* | 6/2018 | Waid .................... E21B 49/088 |
| 2018/0190017 | A1 | 7/2018 | Mendez et al. |
| 2018/0197297 | A1 | 7/2018 | Jia et al. |
| 2018/0202264 | A1 | 7/2018 | Sarduy et al. |
| 2018/0230782 | A1 | 8/2018 | Pankaj et al. |
| 2018/0298746 | A1 | 10/2018 | Short et al. |
| 2018/0315222 | A1 | 11/2018 | Jones |
| 2018/0315232 | A1 | 11/2018 | Jones et al. |
| 2018/0334902 | A1 | 11/2018 | Olsen et al. |
| 2019/0003918 | A1 | 1/2019 | Li et al. |
| 2019/0003919 | A1 | 1/2019 | Asano et al. |
| 2019/0003984 | A1 | 1/2019 | Kester et al. |
| 2019/0103005 | A1 | 4/2019 | Gilberton et al. |
| 2019/0188524 | A1 | 6/2019 | He et al. |
| 2019/0219558 | A1 | 7/2019 | Villar et al. |
| 2019/0220002 | A1 | 7/2019 | Huang et al. |
| 2019/0292908 | A1 | 9/2019 | Karimi et al. |
| 2020/0293828 | A1 | 9/2020 | Wang et al. |
| 2020/0294257 | A1 | 9/2020 | Yoo et al. |
| 2020/0302125 | A1 | 9/2020 | Bei et al. |
| 2020/0332627 | A1 | 10/2020 | Tang et al. |

FOREIGN PATENT DOCUMENTS

| | | |
|---|---|---|
| WO | 2017/180157 A1 | 10/2017 |
| WO | 2018/132786 A1 | 7/2018 |

OTHER PUBLICATIONS

Liu et al., "A Real-Time High Performance Computation Architecture for Multiple Moving Target Tracking Based on Wide-Area Motion Imagery via Cloud and Graphic Processing Units", published Feb. 12, 2017 (Year: 2017).

(56) References Cited

OTHER PUBLICATIONS

Office Action received for U.S. Appl. No. 13/282,282, dated May 11, 2015.
Zhai et al., "Smart Autopilot Drone System for Surface Surveillance and Anomaly Detection via Customizable Deep Neural Network", 2020 (Year: 2020).
Abbaszadeh, M., Corbett, C., Broetz, R., Wang, J., Xue, F., Nitka, T., Zhang, Y., Liu, Z.Y. "Development of an Integrated Reservoir Model for a Naturally Fractured Volcanic Reservoir in China." SPE Reservoir Evaluation and Engineering, Oct. 2001, pp. 406-414. (Year: 2001).
C.S. Kabir, B. Izgec; "Diagnosis of Reservoir Compartmentalization from Measured Pressure/Rate Data during Primary Depletion"; Elsevier, 2009; Journal of Petroleum Science and Engineering, vol. 69; p. 271-282.
Committee on Advanced Drilling Technologies, National Research Council. "Drilling and Excavation Technologies for the Future." The National Academic Press, 1994. (Year: 1994).
Jerry Ham, "Ranking of Texas Reservoirs for Application of Carbon Dioxide Miscible Displacement", Apr. 1996.
Jonas Cordazzo, Colvis Raimundo Maliska, Antonio Fabio Carvalho da Silva; "Interblock Transmissibility Calculation Analysis for Petroleum Reservoir Simulation"; Federal University of Santa Catarina, Nov. 2002; p. 1-18.
Investorwords.com, "lagging indiciator", "leading indicator", http://www.investorwords.com/2713/lagging_indicator.html, http://www.investorwords.com/2741/leading indicator.html.
Priscilla G. McLeroy; "Transient Pressure Analysis in Strip Reservoirs with Linear Skin Discontinuities"; Stanford University, 1986; p. i-58.
Sayarpour M, Zuluaga E, Kabir C S, et al. The use of capacitance-resistance models for rapid estimation of waterflood performance and optimization. Journal of Petroleum Science and Engineering, 2009, 69(3/4): 227-238.
Shunde Yin; "Geomechanics-Reservoir Modeling by Displacement Discontinuity-Finite Element Method"; University of Waterloo, 2008; p. i-141.
Slide from Presentation by Inventor Joe Ault (2003).
U.S. Appl. No. 15/408,397, filed Jan. 17, 2016, Saleri et al.
U.S. Appl. No. 15/618,399, filed Jun. 9, 2017, Saleri et al.
U.S. Appl. No. 15/299,298, filed Oct. 21, 2016, Saleri et al.
U.S. Appl. No. 15/299,828, filed Oct. 21, 2016, Saleri et al.
U.S. Appl. No. 13/282,282, filed Oct. 26, 2011, Notice of Allowance dated Mar. 16, 2017.
U.S. Appl. No. 16/448,594, filed Jun. 21, 2019, by Toronyi.
Zhang, Guohong. Estimating Uncertainties in Integrated Reservoir Studies. Dec. 2003. Texas A&M University, PhD dissertation. (Year: 2003).
Guidelines for the Evaluation of Petroleum Reserves and Resource, 2001 https://www.spe.org/industry/docs/Guidelines-Evaluation-Reserves-Resources-2001 .pdf (Year: 2001).
New Oil in Old Places; Robert M. Sneider and John S. Sneider; Search and Discovery Article #10007 (2000) (Year: 2000).
U.S. Appl. No. 14/836,564, filed Aug. 26, 2015, Mondal et al.
U.S. Appl. No. 12/915,278, filed Oct. 29, 2010, Saleri.
U.S. Appl. No. 12/606,027, filed Oct. 26, 2009, Saleri.
U.S. Appl. No. 13/282,272, filed Oct. 26, 2011, Saleri.
U.S. Appl. No. 15/914,712, filed Mar. 7, 2018, Saleri.
U.S. Appl. No. 15/618,890, filed Jun. 9, 2017, Matringe.
U.S. Appl. No. 16/359,604, filed Mar. 20, 2019, Vajargah.
U.S. Appl. No. 16/389,086, filed Apr. 19, 2019, Benhallam.
U.S. Appl. No. 16/373,053, filed Apr. 2, 2019, Zhai.
Batavia, "Front-End Loading for Life Cycle Success", Offshore Technology Conference Paper No. OTC-12980; Published Apr. 2001.
BDM-Oklahoma, Inc., "Feasability Study of Heavy Oil Recovery in the United States", U.S. Department of Energy, Document No. NIPER/BDM-0225; Published Mar. 1995.
Burns et al., "Gas Field Development: Automatic Selection of Locations for New Producing Wells", Society of Petroleum Engineers, Document No. SPE-2429; Published 1969.
Cordazzo et al., "Interblock Transmissibility Calculation Analysis for Petroleum Reservoir Simulation", Federal University of Santa Catarina, Nov. 2002, pp. 1-18.
Fiksel et al., "Measuring Progress Towards Sustainability Principles, Process, and Best Practices", 1999 Greening of Industry Network Conference Best Practice Proceedings.
Freudenrich, Ph.D., Craig, and Jonathan Strickland, "How Oil Drilling Works" Apr. 12, 2001. HowStuffWorks.com retrieved from WayBack Machine, http://web.archive.org/web/20060418040616/http://science.howstuffworks.com/oil-drilling.htm/printable.
Graf et al., "Candidate Selection Using Stochastic Reasoning Driven by Surrogate Reservoir Models"; Society of Petroleum Engineers, Document No. SPE-136373; SPE Reservoir Evaluation and Engineering; Published Aug. 2011; p. 433-442.
Ham, Jerry, Ranking of Texas Reservoirs for Application of Carbon Dioxide Miscible Displacement, Apr. 1996.
Helman, "The Octopus", Forbes Energy & Genius, pp. 454-51, Nov. 24, 2008.
Investopedia.com, "What are leading, lagging, and coincident indicators? What are they for?", http://www.investopedia.com/ask/answers/177.asp, retrieved on Feb. 27, 2012.
Investorwords.com, "lagging indicator", "leading indicator", http://www.investorwords.com/2713/lagging_indicator.html, http://www.investorwords.com/2741/leading_indicator.html.
Izgec et al., "Quantifying Reservoir Connectivity, In-Place Volumes, and Drainage-Area Pressures during Primary Depletion"; Elsevier, 2009; Journal of Petroleum Science and Engineering, vol. 69; p. 7-17.
Jolley et al., Reservoir Compartmentalization: An Introduction'; Reservoir Compartmentalization; The Geological Society of London, 2010; Special Publications vol. 347; pp. 1-8.
Kabir et al., "Diagnosis and Reservoir Compartmentalization from Measured Pressure/Rate Data during Primary Depletion"; Elsevier, 2009; Journal of Petroleum Science and Engineering, vol. 69, pp. 271-282.
McElroy, "Transient Pressure Analysis in Strip Reservoirs with Linear Skin Discontinuities", Stanford University, 1986, p. 1-58.
"The Report of The BP U.S. Refineries Independent Safety Review Panel", Jan. 2007.
Rivas et al., "Ranking Reservoirs for Carbon Dioxide Flooding Processes", 1994.
Saleri et al., "Data and Data Hierarchy", SPE 21369, pp. 1286-1293, Dec. 1992.
Saleri, "Dawn in the Desert: Saudi High Tech Paying Off at Ghawar", Energy Tribune, pp. 15-17, Sep. 2007.
Saleri et al., "Engineering Control in Reservoir Simulation: Parts I and II", SPE 18305, 1988.
Saleri et al., "The Expanding Role of the Drill Bit in Shaping the Subsurface", JPT, pp. 53-58, Dec. 2003.
Saleri, "Haradh III: A Milestone for Smart Fields", JPT, Nov. 2006.
Saleri, "'Learning' Reservoirs: Adapting to Disruptive Technologies", JPT, pp. 57-60, Mar. 2002.
Saleri, "The Next Trillion: Anticipating and Enabling Game-Changing Recoveries", JPT, Apr. 2006.
Saleri, "Reservoir Management Tenets: Why They Matter to Sustainable Supplies", JPT, pp. 28-30, Jan. 2005.
Saleri, "Reservoir Performance Forecasting: Acceleration by Parallel Planning", JPT, pp. 652-657, Jul. 1993.
Saleri et al., "Shaybah-220: A Maximum-Reservoir-Contact (MRC) Well and Its Implications for Developing Tight-Facies Reservoirs", SPE Reservoir Evaluation &.
Saleri, "Tenets and Diagnostics in Modern Reservoir Management", 8th International Forum on Reservoir Simulation, Jun. 2005, Stressa, Italy.
Sayarpour et al., "The use of capacitance-resistance models for rapid estimation of waterflood performance and optimization", Journal of Petroleum Science and Engineering, 69 (2009, 227-238).
Schlumberger.com retrieved from WayBack Machine, http://web.archive.org/web/20071230014516/http://www.slb.com/.
Slide from 2003 Presentation by Joe Ault.

(56) References Cited

OTHER PUBLICATIONS

Smalley et al., "Reservoir Compartmentalization Assessed with Fluid Compositional Data", Society of Petroleum Engineers, Aug. 1994; SPE Reservoir Engineering, vol. 9 Is. 3; p. 175-180.
Society of Petroleum Engineers, "Petroleum Resources Management System"; SPE/World Petroleum Council; Published Apr. 2007.
Society of Petroleum Engineers, "Guidelines for the Evaluation of Petroleum Reserves and Resources"; SPE in associate with World Petroleum Congresses and American Association of Petroleum Geologists, 2001; pp. 1-139.
Yin "Geomechanics-Reservoir Modeling by Displacement Discontinuity-Finite Element Method" University of Waterloo, 2008, p. 1-141.
U.S. Appl. No. 12/392,891, filed Feb. 25, 2009, Office Action dated Dec. 8, 2010.
U.S. Appl. No. 12/392,891, filed Feb. 25, 2009, Notice of Allowance dated Mar. 24, 2011.
U.S. Appl. No. 12/606,027, filed Oct. 26, 2009, Office Action dated Aug. 10, 2011.
U.S. Appl. No. 12/915,278, filed Oct. 29, 2010, Office Action dated Nov. 7, 2011.
U.S. Appl. No. 12/567,361, filed Sep. 25, 2009, Office Action dated Nov. 30, 2011.
U.S. Appl. No. 12/567,404, filed Sep. 29, 2009, Office Action dated Dec. 8, 2011.
U.S. Appl. No. 12/606,027, filed Oct. 26, 2009, Final Office Action dated Jan. 19, 2012.
U.S. Appl. No. 12/567,361, filed Sep. 25, 2009, Notice of Allowance dated Feb. 2, 2012.
U.S. Appl. No. 12/567,404, filed Sep. 25, 2009, Notice of Allowance dated Feb. 7, 2012.
U.S. Appl. No. 12/915,278, filed Oct. 29, 2010, Final Office Action dated Mar. 1, 2012.
U.S. Appl. No. 13/282,297, filed Oct. 26, 2011, Office Action dated Apr. 1, 2013.
U.S. Appl. No. 13/282,297, filed Oct. 26, 2011, Final Office Action dated Sep. 11, 2013.
U.S. Appl. No. 13/282,297, filed Oct. 26, 2011, Advisory Action dated Nov. 18, 2013.
U.S. Appl. No. 13/282,272, filed Oct. 26, 2011, Office Action dated Mar. 27, 2014.
U.S. Appl. No. 13/282,282, filed Oct. 26, 2011, Office Action dated Mar. 27, 2014.
U.S. Appl. No. 13/282,315, filed Oct. 26, 2011, Office Action dated Aug. 18, 2014.
U.S. Appl. No. 13/282,272, filed Oct. 26, 2011, Office Action dated Nov. 7, 2014.
U.S. Appl. No. 13/282,282, filed Oct. 26, 2011, Final Office Action dated Dec. 26, 2014.
U.S. Appl. No. 13/282,315, filed Oct. 26, 2011, Office Action dated Feb. 18, 2015.
U.S. Appl. No. 13/282,297, filed Oct. 26, 2011, Office Action dated Mar. 16, 2015.
U.S. Appl. No. 13/282,282, filed Oct. 26, 2011, Office Action dated May 11, 2015.
U.S. Appl. No. 13/282,315, filed Oct. 26, 2011, Final Office Action dated Jun. 25, 2015.
U.S. Appl. No. 13/282,282, filed Oct. 26, 2011, Office Action dated Nov. 20, 2015.
U.S. Appl. No. 13/282,282, filed Oct. 26, 2011, Notice of References cited Nov. 30, 2015.
U.S. Appl. No. 13/282,272, filed Oct. 26, 2011, Final Office Action dated Dec. 9, 2015.
U.S. Appl. No. 13/282,297, filed Oct. 26, 2011, Final Office Action dated Dec. 30, 2015.
U.S. Appl. No. 13/282,315, filed Oct. 26, 2011, Office Action dated Mar. 9, 2016.
U.S. Appl. No. 13/282,272, filed Oct. 26, 2011, Office Action dated May 19, 2016.
U.S. Appl. No. 13/282,272, filed Oct. 26, 2011, Final Office Action dated Aug. 23, 2016.
U.S. Appl. No. 13/282,315, filed Oct. 26, 2011, Final Office Action dated Sep. 14, 2016.
U.S. Appl. No. 13/282,297, filed Oct. 26, 2011, Office Action dated Oct. 12, 2016.
U.S. Appl. No. 13/282,282, filed Oct. 26, 2011, Final Office Action dated Nov. 14, 2016.
U.S. Appl. No. 15/299,828, filed Oct. 21, 2016, Office Action dated Aug. 17, 2017.
U.S. Appl. No. 15/299,828, filed Oct. 21, 2016, Notice of Allowance dated Feb. 2, 2018.
U.S. Appl. No. 13/282,297, filed Oct. 26, 2011, Notice of Allowance dated May 31, 2017.
U.S. Appl. No. 14/604,367, filed Jan. 23, 2015, Office Action dated Jun. 16, 2017.
U.S. Appl. No. 14/604,330, filed Jan. 23, 2015, Office Action dated Jun. 30, 2017.
U.S. Appl. No. 14/604,367, filed Jan. 23, 2015, Final Office Action dated Sep. 21, 2017.
U.S. Appl. No. 15/618,399, filed Jun. 9, 2017, Office Action dated Apr. 29, 2019.
U.S. Appl. No. 15/618,399, filed Jun. 9, 2017, Notice of Allowance dated Aug. 26, 2019.
U.S. Appl. No. 14/836,564, filed Aug. 26, 2015, Office Action dated Aug. 9, 2018.
U.S. Appl. No. 14/836,564, filed Aug. 26, 2015, Final Office Action dated Feb. 15, 2019.
U.S. Appl. No. 14/836,564, filed Aug. 26, 2015, Notice of Allowance dated Nov. 20, 2019.
U.S. Appl. No. 15/618,890, filed Jun. 9, 2017, Office Action dated Mar. 4, 2019.
U.S. Appl. No. 15/618,890, filed Jun. 9, 2017, Notice of Allowanced dated Jun. 24, 2019.
Rohlfing, T. (Jul. 2001). Efficient voxel lookup in nonuniformly spaced images using virtual uniform axes. In Medical Imaging 2001: Image Processing (vol. 4322, pp. 986-994). SPIE. (Year: 2001).
International Search Report cited in PCT/US2011/030940 dated Jan. 11, 2012.
Final Office Action received for U.S. Appl. No. 16/373,053, dated Feb. 25, 2021, 24 pages.
Hoffimann, Sequence Mining and Pattern Analysis in Drilling Reports with Deep Natural Language Processing, arXiv:1712.01476v1 , Dec. 5 (Year: 2017).
IMRSV, Semantic Averaging of Documents Using WORD2VEC Representations, May 12, 2017, https://imrsv.ai/blog/2017/5/12/semantic-averaging-of-documents-using-word2vec-representations#:~:text=Introduction,are%20most%20likely%20to%20appear. (Year: 2017).
Non-Final Office Action received for U.S. Appl. No. 16/373,053, dated Oct. 14, 2020, 18 pages.
Notice of Allowance received for U.S. Appl. No. 15/914,712, dated Oct. 8, 2020.
Requirement for Restriction/Election received for U.S. Appl. No. 16/373,053, dated Aug. 7, 2020, 6 pages.
Gou et al, CN 108756848, "An Intelligent Drilling Control Cloud Platform and Intelligent Drilling Control System" (translation), May 21, 2019, 17 pgs <CN_108756848.pdf>.

* cited by examiner

Reservoir Management Scorecard 400

| Waterflood Scoring | | Metric | Points | Min=0 | Max=1 | Field Data | Points Awarded |
|---|---|---|---|---|---|---|---|
| Production Performance 401 | | current ave. pI / PI @ peak | 6.67 | <10% | >80% | | |
| | | % EUR produced on plateau | 6.67 | <20% | >60% | | |
| | | Observed field decline (5 Year Average) | 6.67 | >25% | <0% | | |
| Pressure Management 402 | | P / Pi | 15.0 | <30% | >90% | | |
| | | Cum VRR (proxy if p/pi is unavailable) | 5.0 | <10% | >80% | | |
| Water Management 403 | | Δ WCUT per year (3 years trend) | 10.0 | >05% | <1.0% | | |
| | | Water Injection Efficiency | 10.0 | <20% | >80% | | |
| Gas Management 404 | | Production GOR / (Solution GOR x 1.1) | 10.0 | >02% | <1.1 | | |
| | | % Wells with GOR <= Solution GOR x 1.1 | 10.0 | <10% | >80% | | |
| Recovery Efficiency 405 | | EURF / EURF Benchmark | 20.0 | <40% | >90% | | |
| Total Score 406 | | | 100.0 | | | | |

*Figure 4*

| Reservoir Management Competency Score 500 | | |
|---|---|---|
| Production Performance (0-20)  501 | ◯ | 9.9 |
| Pressure Management (0-20)  502 | ◯ | 8.5 |
| Water Management (0-20)  503 | ◯ | 17.6 |
| Gas Management (0-20)  504 | ◯ | 0.7 |
| Recovery Efficiency (0-20)  505 | ◯ | 9.8 |
| Final Score (0-100)  506 | ◯ | 46.5 |
Reservoir Management Competency
 Excellent
 Fair
 Poor
*Figure 5*

FRAMEWORK AND INTERFACE FOR ASSESSING RESERVOIR MANAGEMENT COMPETENCY

CROSS-REFERENCE TO RELATED APPLICATIONS

This application claims the benefit of U.S. Provisional Patent Application Ser. No. 62/690,187, filed Jun. 26, 2018, which is expressly incorporated herein by reference in its entirety.

BACKGROUND

Hydrocarbon extraction sites typically include drilling rigs, completion rigs and other equipment for extracting oil and other materials from the ground. These rigs and associated equipment consume large amounts of manpower dedicated to maintaining and managing the rigs. Typical reservoir management solutions rely heavily on user input (i.e. expert input). For instance, an expert in pressure management may provide input regarding past, current and predicted pressures within a well, an expert in water management may provide input regarding water cut, an expert in gas management may provide input regarding the production gas to oil ratio (GOR), and so on. As these expert opinions are highly prevalent in any reservoir management scheme, and are often subject to bias, there exists a large potential for error when managing a hydrocarbon extraction site.

BRIEF SUMMARY

Embodiments described herein are directed to methods, systems and user interfaces for assessing reservoir management competency for a petroleum producing field. In one embodiment, a computer system measures, using various hardware-based sensors positioned in a petroleum reservoir supplying the petroleum producing field, physical or geological characteristics of the petroleum reservoir. The computer system establishes a reservoir management competency scoring system that evaluates a specific set of objective criteria that reflect a level of reservoir management competency at the petroleum producing field, and automatically generates, according to the objective set of criteria of the reservoir management competency scoring system, a reservoir management rating for the petroleum reservoir based at least in part on data measured by the sensors placed in the petroleum reservoir. Then, based on the generated reservoir management rating, the computer system controls operation of production units configured to direct extraction operations at the petroleum producing field.

In another embodiment, a user interface is provided which includes the following: an interactive production performance indicator configured to illustrate a production performance rating for a petroleum producing field. The production performance rating is based on data captured at the petroleum producing field by various hardware-based sensors. The user interface further includes an interactive pressure management indicator configured to illustrate a pressure management rating for the petroleum producing field. The pressure management rating indicates a ratio of current pressure to initial pressure in the petroleum producing field. The user interface also has an interactive water management indicator configured to illustrate a water management rating for the petroleum producing field, where the water management rating indicates a change in water cut over a specified time.

The user interface further includes an interactive gas management indicator configured to illustrate a gas management rating for the petroleum producing field, where the gas management rating indicates a ratio of production gas-to-oil ratio (GOR) to solution GOR. Also in the user interface is an interactive recovery efficiency indicator configured to illustrate a recovery efficiency rating for the petroleum producing field. The recovery efficiency rating indicates a ratio of an estimated ultimate recover (EUR) to a specified EUR benchmark. A summary indicator in the user interface provides an overall score for reservoir management competency at the petroleum producing field. The summary indicator includes a combination of scores from the production performance, pressure management, water management, gas management and recovery efficiency indicators. The user interface also has a control element that allows control over operation of production units at the petroleum producing field according to the summary indicator.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description, or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which:

FIG. 4 illustrates an alternative embodiment of a user interface that provides a reservoir management score in multiple categories;

FIG. 5 illustrates an alternative embodiment of a user interface that provides a reservoir management score in multiple categories;

DETAILED DESCRIPTION

Figure 1:
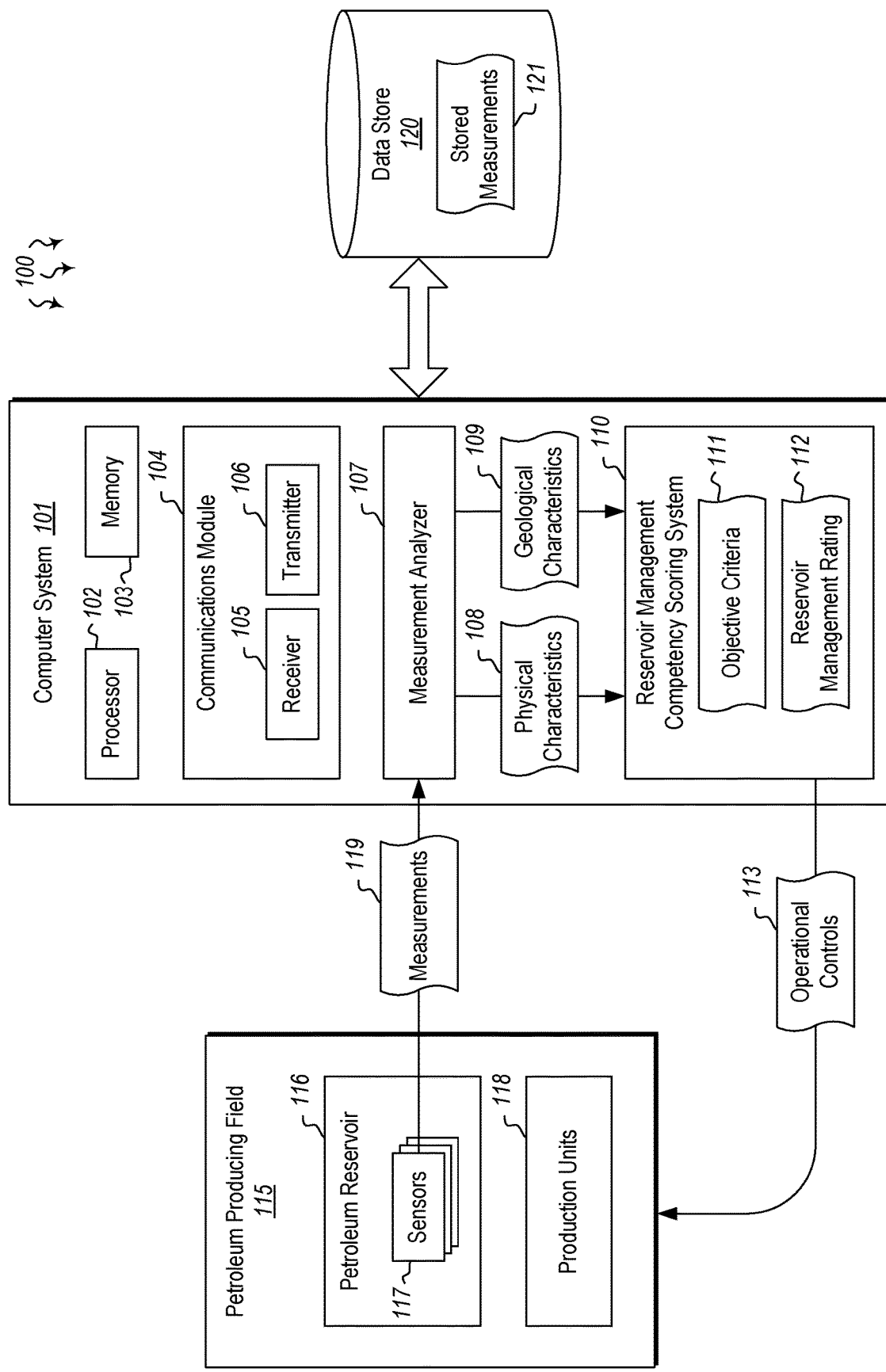
FIG. 1 illustrates a computer architecture in which embodiments described herein may operate including assessing reservoir management competency for a petroleum producing field.

Embodiments described herein are directed to methods, systems and user interfaces for assessing reservoir management competency for a petroleum producing field. In one embodiment, a computer system measures, using various hardware-based sensors positioned in a petroleum reservoir supplying the petroleum producing field, physical or geological characteristics of the petroleum reservoir. The computer system establishes a reservoir management competency scoring system that evaluates a specific set of objective criteria that reflect a level of reservoir management competency at the petroleum producing field, and automatically generates, according to the objective set of criteria of the reservoir management competency scoring system, a reservoir management rating for the petroleum reservoir based at least in part on data measured by the sensors placed in the petroleum reservoir. Then, based on the generated reservoir management rating, the computer system controls operation of production units configured to direct extraction operations at the petroleum producing field.

In another embodiment, a user interface is provided which includes the following: an interactive production performance indicator configured to illustrate a production performance rating for a petroleum producing field. The production performance rating is based on data captured at the petroleum producing field by various hardware-based sensors. The user interface further includes an interactive pressure management indicator configured to illustrate a pressure management rating for the petroleum producing field. The pressure management rating indicates a ratio of current pressure to initial pressure in the petroleum producing field. The user interface also has an interactive water management indicator configured to illustrate a water management rating for the petroleum producing field, where the water management rating indicates a change in water cut over a specified time.

The user interface further includes an interactive gas management indicator configured to illustrate a gas management rating for the petroleum producing field, where the gas management rating indicates a ratio of production gas-to-oil ratio (GOR) to solution GOR. Also in the user interface is an interactive recovery efficiency indicator configured to illustrate a recovery efficiency rating for the petroleum producing field. The recovery efficiency rating indicates a ratio of an estimated ultimate recover (EUR) to a specified EUR benchmark. A summary indicator in the user interface provides an overall score for reservoir management competency at the petroleum producing field. The summary indicator includes a combination of scores from the production performance, pressure management, water management, gas management and recovery efficiency indicators. The user interface also has a control element that allows control over operation of production units at the petroleum producing field according to the summary indicator.

Embodiments of the present invention may comprise or utilize a special-purpose or general-purpose computer system that includes computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the invention can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud-computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Some embodiments, such as a cloud-computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

Still further, system architectures described herein can include a plurality of independent components that each contribute to the functionality of the system as a whole. This modularity allows for increased flexibility when approaching issues of platform scalability and, to this end, provides a variety of advantages. System complexity and growth can be managed more easily through the use of smaller-scale parts with limited functional scope. Platform fault tolerance is enhanced through the use of these loosely coupled modules. Individual components can be grown incrementally as business needs dictate. Modular development also translates to decreased time to market for new functionality. New functionality can be added or subtracted without impacting the core system.

Referring to the figures, FIG. 1 illustrates a computer architecture 100 in which at least one embodiment described herein may be employed. The computer architecture 100 includes a computer system 101. The computer system 101 includes at least one processor 102 and at least some system memory 103. The computer system 101 may be any type of local or distributed computer system, including a cloud computer system. The computer system 101 includes modules for performing a variety of different functions. The program modules may be hardware-based, software-based, or a combination thereof. Each program module uses computing hardware and/or software to perform functions including those defined herein below.

For instance, communications module 104 may be configured to communicate with other computer systems. The communications module 104 may include any wired or wireless communication means that can receive and/or transmit data to or from other computer systems. The communications module 104 may include, for example, a hardware receiver 105 and a hardware transmitter 106. These radios may be WiFi, Bluetooth, cellular, GPS or other types of radios. The communications module 104 may be configured to interact with databases, mobile computing devices (such as mobile phones or tablets), embedded or other types of computer systems.

The computer system 101 may be configured to communicate with and receive information from petroleum producing field 115. For instance, the computer system 101 may receive measurements 119 from sensors 117 on the petroleum reservoir 116. The sensors may be pressure sensors, movement sensors, flow sensors, temperature sensors, radiation sensors or other types of hardware sensors. The measurement analyzer 107 of computer system 101 may receive these measurements 119 on a continual basis (and in some cases, on a scheduled basis). The measurement analyzer 107 may be configured to analyze measurements received from the sensors, or may be configured to perform the measurements using the sensors 117.

Thus, the measurement analyzer 107 may measure, using the hardware-based sensors 117 positioned in the petroleum reservoir 116 supplying the petroleum producing field 115, physical 108 or geological characteristics 109 of the petroleum reservoir. These physical or geologic characteristics may include an indication of geological layers, rock types, well depths, conductivity between wells, location, elevation or other physical or geological characteristics of a well.

The computer system 101 may include (or may instantiate on another computer system) a reservoir management competency scoring system 110. The reservoir management competency scoring system 110 may be configured to evaluate a specific set of objective criteria that reflect a level of reservoir management competency at a given petroleum producing field (e.g. 115). The reservoir management competency scoring system 110 is, at least in some embodiments, a purely objective scoring system that is operated without receiving input from experts or other users. This allows the reservoir management competency scoring system 110 to be completely unbiased in its score assessment. The objective criteria 111, as will be described further below, provide indications of how well a given petroleum producing field or petroleum reservoir is being managed. Poorly managed reservoirs cost petroleum producers millions of dollars each year. Thus, even small improvements in field management can yield large results.

The reservoir management competency scoring system 110 may include, or may itself be, a rating generator. The rating generator may be configured to automatically generate, according to the objective set of criteria 111, a reservoir management rating 112 for the petroleum reservoir 116 based at least in part on data measured by the sensors 117 placed in the petroleum reservoir (i.e. measurements 119). Once this rating 112 has been generated, an operations control unit (or the reservoir management competency scoring system itself) may generate operational controls 113 that control operation of one or more production units 118 at the petroleum producing field 115. The operations of the production units are controlled according to the generated reservoir management rating 112. These control direct extraction operations at the petroleum producing field 115. In this manner, the reservoir management competency scoring system 110 can not only generate a reservoir management rating 112 that helps managers know how to better manage any given petroleum reservoir, but also directly control operations of the reservoir based on the rating. These concepts will be explained further below with regard to the user interfaces of FIGS. 2-6, and with regard to method 700 of FIG. 7.

Figure 2:
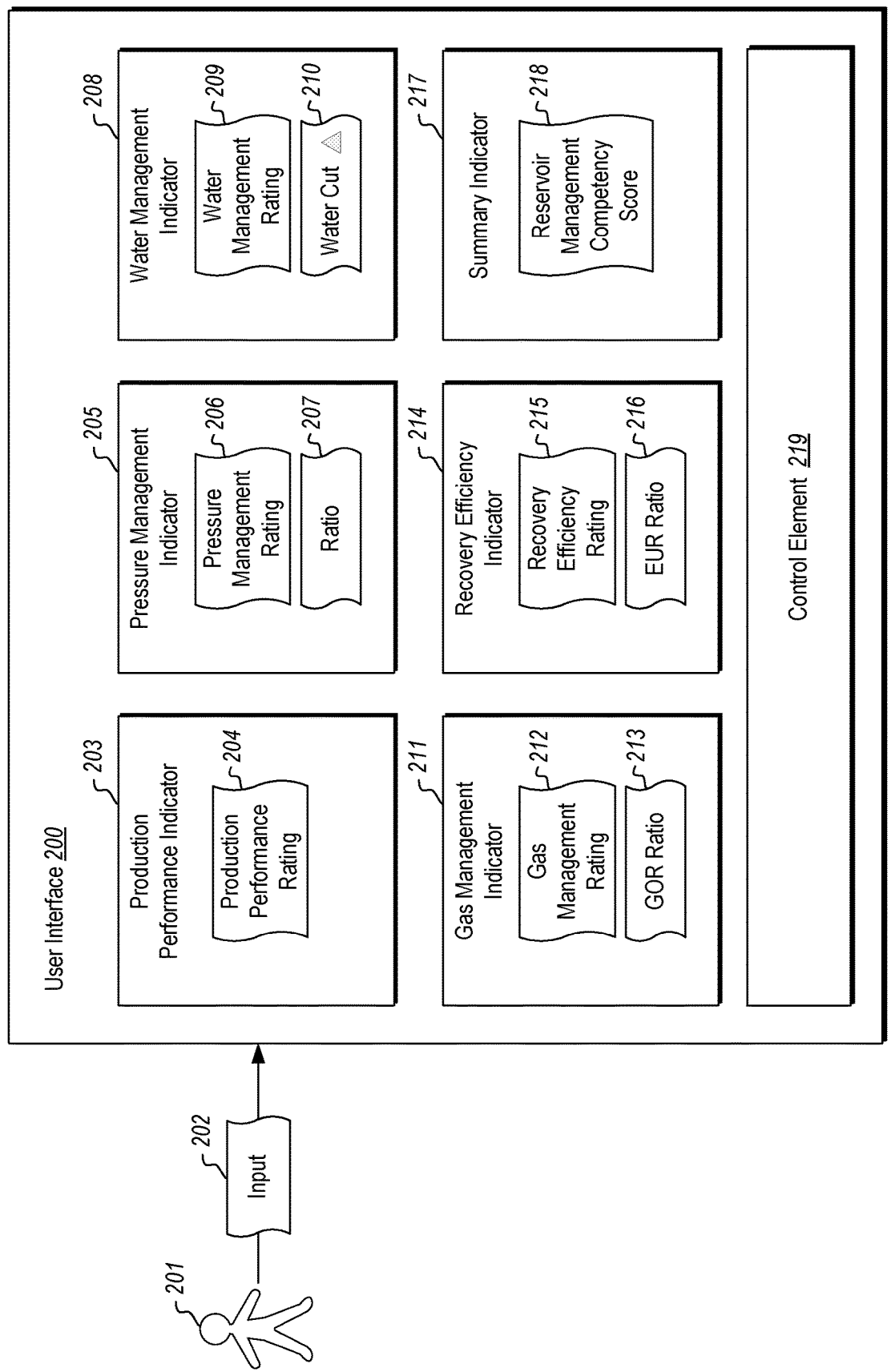
FIG. 2 illustrates an embodiment of a user interface that provides a reservoir management competency assessment.

FIG. 2 illustrates a user interface 200 that has multiple different indicators, as well as a control element 219. The control indicators include a production performance indicator 203, a pressure management indicator 205, a water management indicator 208, a gas management indicator 211, a recovery efficiency indicator 214, and a summary indicator 217. While these six indicators are described herein in conjunction with user interface 200, it will be understood that substantially any number of different indicators and different combinations may be used and displayed within the user interface.

In one embodiment, a computer program product is provided that includes computer storage media having thereon computer-executable instructions that, when executed by processor 101 of computer system 100, for example, cause the computer system to instantiate the user interface 200. As shown in FIG. 2, the user interface 200 (or UI 200 herein) includes an interactive production performance indicator 203. This interactive production performance indicator provides a production performance rating 204 for a petroleum producing field (e.g. 115). The production performance rating is based on data captured at the petroleum producing field by various hardware-based sensors 117. The production performance rating 204 indicates how well the reservoir is currently doing compared to past production performance measurements, and perhaps relative to other petroleum reservoirs within the petroleum producing field 115 or neighboring fields. The production performance rating 204 may include an indication of the amount of material (e.g. oil and gas) being produced. This amount may be an hourly, daily, monthly or other amount. The production rating may take into account past performance of the reservoir or field, and from that prior rating, determine whether current production is adequate or inadequate.

Figure 3:
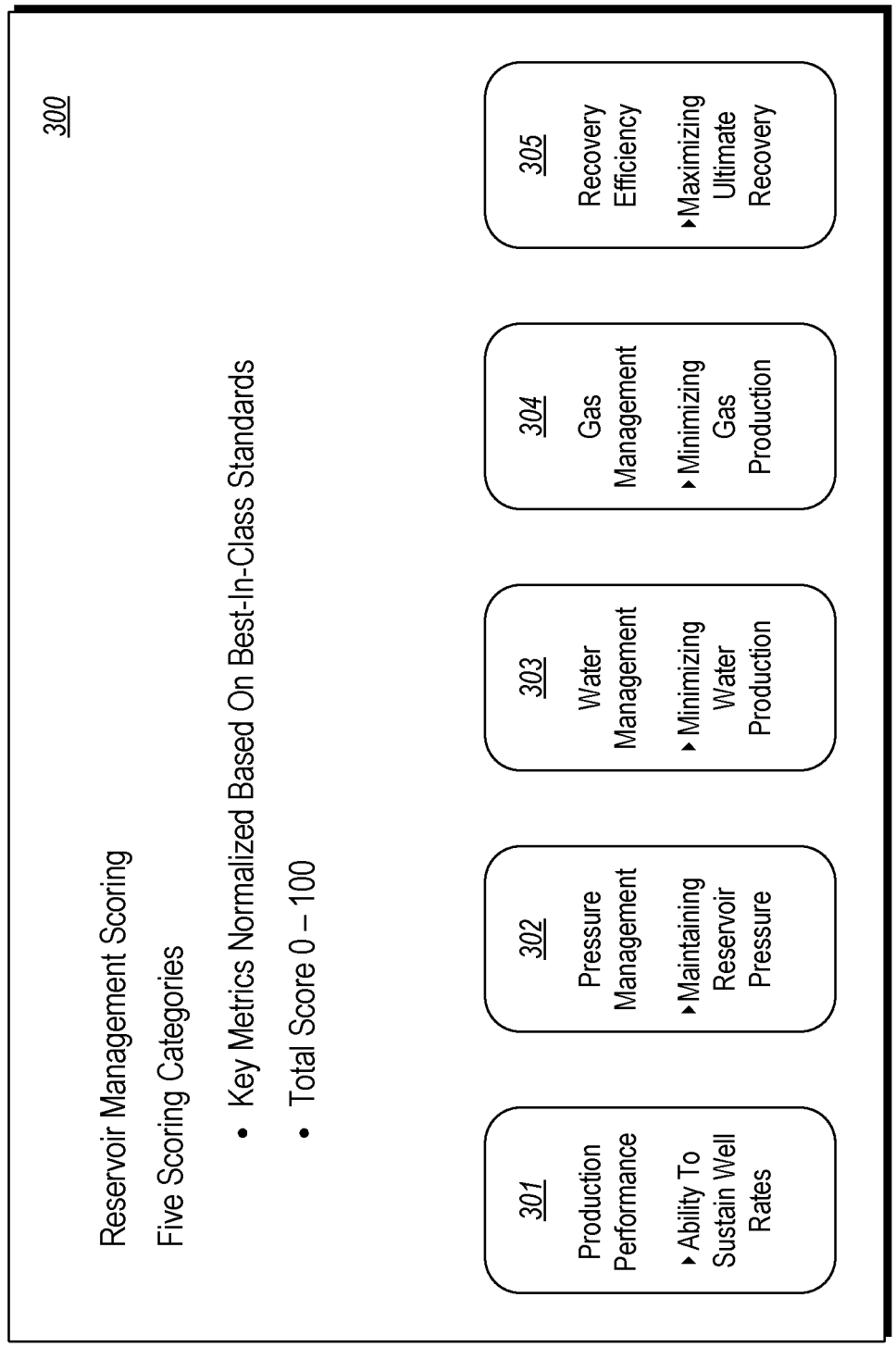
FIG. 3 illustrates an embodiment of a user interface that provides a reservoir management score in multiple categories.

As shown in UI 300 of FIG. 3, in some embodiments, a total reservoir management score may include the five categories previously mentioned: production performance 301, pressure management 302, water management 303, gas management 304, and recovery efficiency 305. Each of these categories may be assigned 20 total points, such that the overall maximum score is 100. Of course, other numbering or ranking systems may be used. Based on the criteria identified above for production performance, including the ability for the reservoir to sustain current production rates, a 0-20 score is assigned for production performance.

UI 400 of FIG. 4 shows greater detail for each of the indicators, including production performance 401. In this embodiment, production performance is broken up into three categories, each having 6.67 points for a total of 20. One category is the current average production compared to a peak production rate. Another category is the percentage of expected ultimate recovery (EUR) on the petroleum producing field. Still further, the third category is the average observed field decline over five years. Again, other such categories or subcategories may be used to generate the overall indicator score. Red, yellow, green or other colors or symbols may be included in the UI, such that a user can view, at a glance, which indicator categories are performing well, and which are performing poorly.

Returning to UI 200 of FIG. 2, the interactive pressure management indicator 205 may be configured to illustrate a pressure management rating 206 for the petroleum producing field 115. The pressure management rating 206 indicates a ratio 207 of current pressure to initial pressure in the petroleum producing field. This ratio, as shown in element 302 of FIG. 3, and 402 of FIG. 4, can include not only the current pressure to initial pressure ratio which helps in managing pressure in the well, but also the cumulative voidage replacement ratio (VRR). In some embodiments, the P/Pi ratio may be weighted more heavily than the cumulative VRR. Indeed, as shown in UI 400 of FIG. 4, the P/Pi ratio is assigned 15 points, while the cumulative VRR is assigned five points, for a total of 20 points. Substantially any category weighting may be used, based on the relative importance of the indicator to the user 201. In some cases, the user 201 may be able to provide input 202 that changes the weighting of any subcategory (e.g. assigning one subcategory 12 points and the other subcategory 8 points) or any category (e.g. assigning pressure management 30 points, while reducing production performance to 10 points). Any such combinations thereof are contemplated herein.

UI 200 of FIG. 2 next includes an interactive water management indicator 208, which illustrates a water management rating 209 for the petroleum producing field 115. The water management rating 209 indicates a change in water cut 210 over a specified time. The water cut 210 represents a ratio of water produced versus oil produced. As noted in element 303 of UI 300, the water management indicator indicates how well the reservoir is doing at minimizing water production. The change in water cut over time can indicate whether the amount of water being produced as compared to the amount of oil is increasing or decreasing. As further noted in element 403 of FIG. 4, the water management indicator may include an indication of water injection efficiency that measures how much water has been injected versus oil extracted from the petroleum reservoir 116. Again, twenty points may be assigned to this indicator, with 10 points going to each subcategory.

The gas management indicator 211 of FIG. 2 illustrates a gas management rating 212 for the petroleum producing field 115. The gas management rating 212 indicates a ratio of production gas-to-oil ratio (GOR) to solution GOR 213. This ratio will be explained further below, but generally indicates whether gas production is being minimized at the well. A numeric or colored indicator may be displayed (e.g. 304 of FIG. 3, or 404 of FIG. 4) to show how well the reservoir is doing at minimizing gas production and, correspondingly, maximizing oil production.

The interactive recovery efficiency indicator 214 of UI 200 illustrates a recovery efficiency rating 215 for the petroleum producing field 115. The recovery efficiency rating 215 indicates a ratio 216 of an estimated ultimate recover (EUR) to a specified EUR benchmark. This ratio assesses whether the reservoir is above, at or below the EUR benchmark. All wells decline in production over time. This EUR benchmark allows a comparison to be made between similar production decline curves and the production decline curve for this well. The summary indicator 217 provides an overall score 218 for reservoir management competency at the petroleum producing field 115. The summary indicator includes a combination of scores from each of the five indicators: the production performance, pressure management, water management, gas management and recovery efficiency indicators.

The control element 219 allows the user 201 to make control changes to the production units 118 at the reservoir based on the overall score by interacting with the control element 219 to cause the operational controls 113 to be sent to the production units 118. In some cases, the changes to the production units occur automatically as a result of the operational controls 113 being sent to the production units 118, depending on the score. For instance, if a certain category's score is low enough, a corresponding production unit change may be automatically carried out. Thus, for example, if the gas management score is below a threshold level, operation controls (such as controls 113) may be automatically generated and sent to the production unit to change pump speeds, drill speeds, drill locations, injection rates, or other physical controls that affect the GOR. Many other such embodiments are possible. The user 201 may be able to set the threshold level, in the control element 219, for each indicator below which certain actions will be taken automatically. The user may also be able to specify which actions are taken at each threshold. Thus, if an indicator's score continues to drop and reach new thresholds, certain actions may be taken automatically by the system at each threshold to raise the score.

In some embodiments, these actions may be initiated using the control element 219 of UI 200. The control element may directly control one or more operations on the production units 118, or may provide access to a menu where automatic actions are selected or created. Thus, the control element 219 can automatically provide operational commands to the various production units. The commands may be sent as a one-time event, or periodically once a specific overall score of the summary indicator has been hit. The UI 200 allows users to interact with each indicator (203, 205, 208, 211, 214 or 217) to view a representation of underlying calculations for that indicator. Such a representation is generally shown in UI 400 of FIG. 4, which shows various subcategories and other computations that underlie each indicator, although more or fewer calculations or subcategories may be shown.

Figure 6:
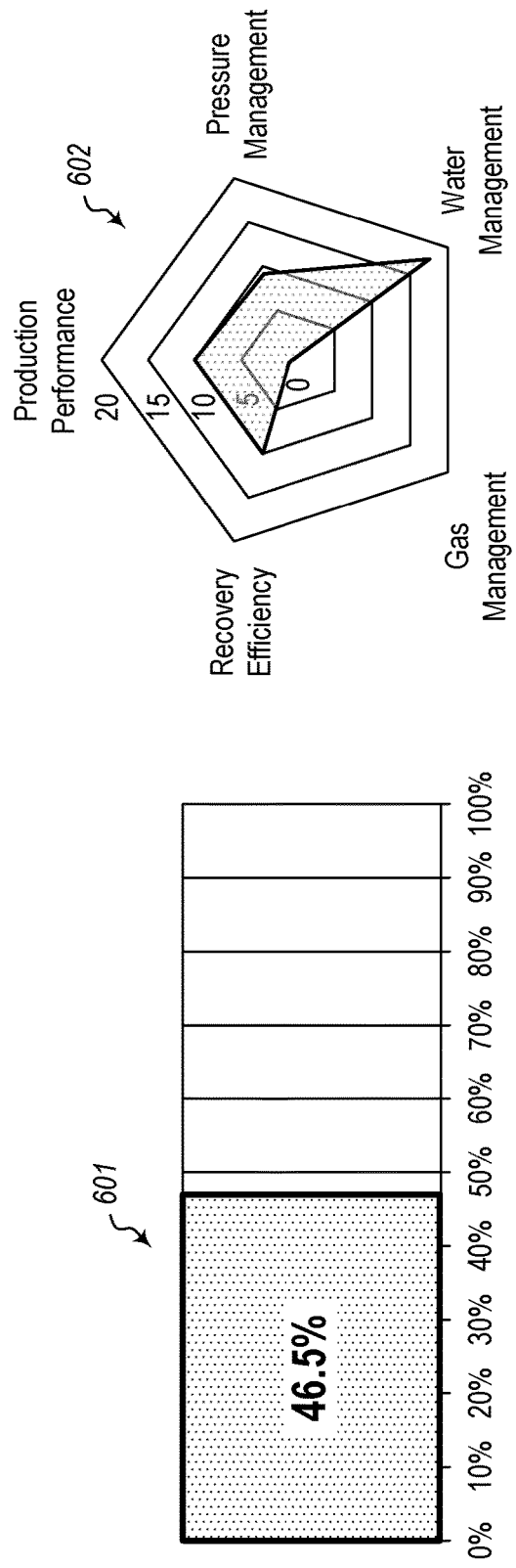
FIG. 6 illustrates an embodiment of a user interface that provides a reservoir management summary.

UI 500 of FIG. 5 shows a simplified embodiment of a reservoir management assessment scoring system. An excellent, fair or poor indicator may be illustrated next to each of the scoring categories including production performance 501 (rated as poor), pressure management 502 (rated as excellent), water management 503 (rated as poor), gas management 504 (rated as poor), recovery efficiency 505 (rated as poor) and the final score 506 (rated as poor). Using this simplified UI, a user may be able to easily see which aspects of the reservoir are doing well, and which are doing poorly. UI 600 of FIG. 6 shows bar graphs (601), plot graphs (602), and summary elements (603) that help to further indicate to a user how well a reservoir is performing. The user interface may include color and design schemes that allow a user to view and understand the summary indicator and combination of scores. These scores can then be used to better manage operations at the reservoir.

Figure 7:
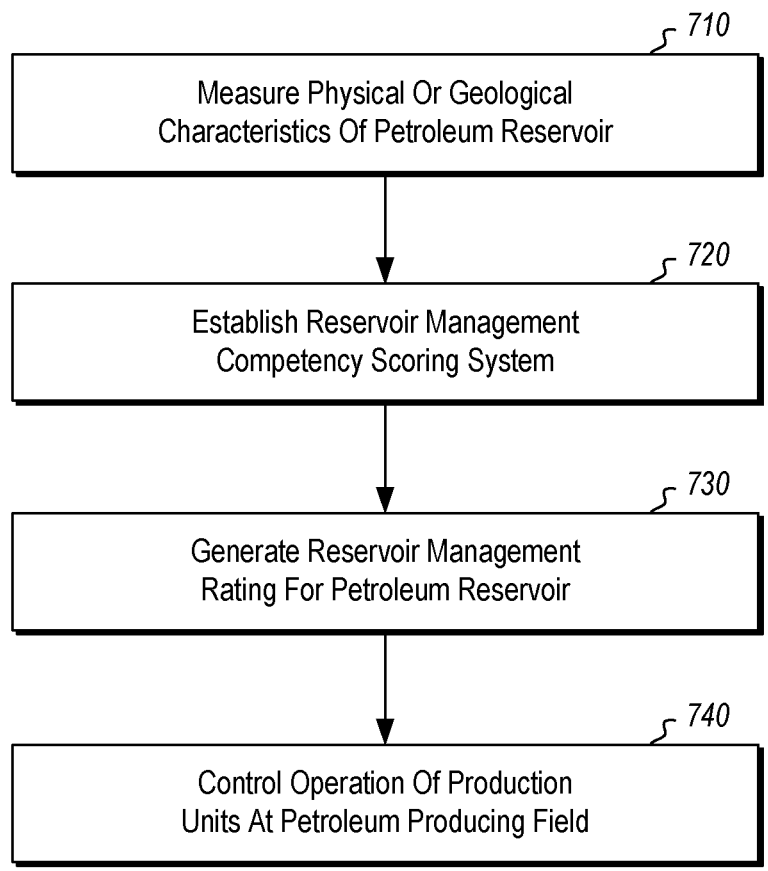
FIG. 7 illustrates a flowchart of an example method for assessing reservoir management competency for a petroleum producing field.

In view of the systems and architectures described above, methodologies that may be implemented in accordance with the disclosed subject matter will be better appreciated with reference to the flow chart of FIG. 7. For purposes of simplicity of explanation, the methodologies are shown and described as a series of blocks. However, it should be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

FIG. 7 illustrates a flowchart of a method 700 for assessing reservoir management competency for a petroleum producing field. The method 700 will now be described with frequent reference to the components and data of environment 100 of FIG. 1.

Method 700 includes measuring, using one or more hardware-based sensors positioned in a petroleum reservoir supplying the petroleum producing field, physical or geological characteristics of the petroleum reservoir (710). For example, measurement analyzer 107 of computer system 100 may measure or otherwise identify physical, geological or other characteristics of the petroleum reservoir 116 based on the data received from the sensors 117. This measurement data 119 may indicate how various portions of production equipment are operating, or how efficiently the reservoir is producing material.

The physical 108 or geological characteristics 109 of the petroleum reservoir 116 may directly or indirectly relate to at least one or more of the following: reservoir pressure, fluid saturation, well productivity and drawdown, fluid profile, oil production, gas production, water production, injection rate, displacement efficiency, sweep efficiency, bypassed petroleum, gas breakthrough, water breakthrough, depletion rate, compartmentalization, vertical and/or horizontal discontinuity, reservoir thickness, reservoir permeability, permeability, fluid viscosity, reservoir depth, sand problems, or other reservoir characteristics.

Method 700 next includes establishing a reservoir management competency scoring system that evaluates a specific set of objective criteria that reflect a level of reservoir management competency at the petroleum producing field (720). The computer system 101 may establish or instantiate reservoir management competency scoring system 110. The reservoir management competency scoring system 110 is configured to evaluate production and management efficiency at the reservoir based on objective criteria 111. New measurement data 119, as well as previously stored measurement data 121 may be used when analyzing the data using the objective criteria.

Based on this analysis, the reservoir management competency scoring system 110 generates a reservoir management rating 112 for the petroleum reservoir based at least in part on data measured by the sensors 117 placed in the petroleum reservoir (730). Then, based on the generated reservoir management rating 112, the reservoir management competency scoring system 110 controls operation of one or more production units 118 that direct extraction operations at the petroleum producing field (740). The production units 118 that are controlled by the reservoir management competency scoring system 110 may include producing oil wells, water injection wells, gas injection wells, heat injectors, or sub-components of the production units. In at least some embodiments, controlling the operation of the production units may include controlling change in volume, change in pressure, change in temperature, change in well bore path, drilling new production units, implementing peripheral water flooding, re-activating an existing well, or shutting down existing production units. Other control operations may also be performed, and the above-identified list is not intended to be limiting.

The reservoir management rating 112 generated by the reservoir management competency scoring system 110 is generated objectively, without expert opinions or interpretations. In other words, at least in some embodiments, the reservoir management rating 112 may be generated without any user input, including expert opinion input. Objective criteria 111 are used which can be implemented at any reservoir worldwide to provide unbiased management efficiency results. The input data is taken from hardware sensors 117 installed at the petroleum reservoir 116. These sensors capture pressure data, gas data, water ratings, material production rate and other physical measurements at the petroleum producing field 115. The reservoir management competency scoring system 110 evaluates any one or more of the following with respect to the petroleum reservoir: production performance, pressure management, water management, gas management and/or recovery efficiency.

The production performance indicates a comparison of current average productivity compared to peak productivity (P/Pk ratio). This identifies the amount of material the petroleum reservoir is currently producing versus the amount the petroleum reservoir has produced over a past period of time. The production performance indicator (e.g. 203 of FIG. 2) may further take into account production levels at different petroleum reservoirs within the petroleum producing field, identifying an amount of material recovered at other petroleum reservoirs within the petroleum producing field. If the reservoir 116 is producing an amount far below other reservoirs in the field 115, it can be determined that production efficiency may be improved in some manner.

The pressure management (e.g. 205 of FIG. 2) indicates a measurement of current pressure over initial pressure (P/Pi ratio). This results in a cumulative voidage replacement ratio (VRR) that indicates a ratio of total volume extracted over a specified time frame (e.g. over five years). The water management (e.g. 208 of FIG. 2) indicates a change in water cut over a specified time frame. The water cut is a ratio of water produced versus oil produced, and is an indication of water injection efficiency that measures how much water has been injected versus oil extracted from the petroleum reservoir.

The gas management (e.g. 211 of FIG. 2) indicates a comparison of production gas-to-oil ratio (GOR) and solution GOR. The comparison illustrates how much of the produced gas is solution versus how much of the produced gas is outside of the solution of gas in the petroleum reservoir. In some embodiments, the solution GOR is multiplied by 1.1. In this case then, the GOR metric is the percentage of wells with a GOR exceeding the solution GOR by a factor of 1.1, thereby providing a 10% variation due to measurement error. The recovery efficiency (e.g. 214 of FIG. 2 indicates a comparison of expected ultimate recovery (EUR) to a specified benchmark amount. The EUR indicates an approximation of an amount of oil or gas that is potentially recoverable or has already been recovered from the petroleum reservoir. The summary indicator (e.g. 217 of FIG. 2) indicates a total score for each of the indicators. This score may trigger certain actions at the production units 118 to control operations and increase their operational efficiency.

In some embodiments, the computer system 101 may generate an interactive scorecard based on the reservoir management rating 112. This interactive scorecard indicates how effective a company's reservoir management currently is, and allows users to drill down into underlying causes for the rating. For instance, in such an interactive scorecard, the user could drill down on production performance and see which specific subcategories, formulas, equations or other criteria were causing the production performance to be overly high or low. In conjunction with the interactive scorecard, the computer system 101 may also generate a partial company valuation based on the scorecard indication of how well the reservoir is being managed. This company valuation may higher if the reservoir is being properly and efficiently managed, and lower if the reservoir is being poorly and inefficiently managed. Capital costs and operating costs may also be taken into consideration when generating this valuation.

Accordingly, methods, systems and computer program products are provided which assessing reservoir management competency for a petroleum producing field. User interface embodiments are provided which allow the user to view a variety of different objective indicators that each shed light on how well a reservoir is being managed. The user interface also allows users to make changes to production parameters and operations at the petroleum producing field. These changes can increase the effectiveness, efficiency and overall output of the well by improving specific areas of well management.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

The invention claimed is:

1. A method, implemented at a computer system that includes at least one processor, for assessing reservoir management competency for a petroleum producing field, the method comprising:
   measuring, using one or more hardware-based sensors positioned in a petroleum reservoir supplying the petroleum producing field, physical or geological characteristics of the petroleum reservoir;
   establishing a reservoir management competency scoring system that evaluates a specific set of objective criteria that reflect a level of reservoir management competency at the petroleum producing field, wherein the reservoir management competency scoring system includes a gas management rating that indicates a ratio of production gas-to-oil ratio (GOR) to solution GOR;
   automatically generating, according to the objective set of criteria of the reservoir management competency scoring system, a reservoir management rating for the petroleum reservoir based at least in part on data measured by the one or more sensors placed in the petroleum reservoir; and
   based on the generated reservoir management rating, controlling operation of one or more production units configured to direct extraction operations at the petroleum producing field.

2. The method of claim 1, wherein the one or more production units comprise at least one of producing oil wells, water injection wells, gas injection wells, heat injectors, or one or more sub-components of the one or more production units, and wherein controlling the operation of the one or more production units comprises causing at least one of change in volume, change in pressure, change in temperature, change in well bore path, drilling one or more new production units, implementing peripheral water flooding, re-activating an existing well, or shutting down one or more existing production units.

3. The method of claim 1, wherein the physical or geological characteristics of the petroleum reservoir directly or indirectly relate to at least one of reservoir pressure, fluid saturation, well productivity and drawdown, fluid profile, oil production, gas production, water production, injection rate, displacement efficiency, sweep efficiency, bypassed petroleum, gas breakthrough, water breakthrough, depletion rate, compartmentalization, vertical and/or horizontal discontinuity, reservoir thickness, reservoir permeability, permeability, fluid viscosity, reservoir depth, or sand problems.

4. The method of claim 1, wherein the reservoir management rating is generated objectively, without expert opinions or interpretations.

5. The method of claim 1, wherein the hardware sensors are configured to capture pressure data, gas data, water ratings and production rate at the petroleum producing field.

6. The method of claim 1, wherein the reservoir management competency scoring system evaluates one or more of the following with respect to the petroleum reservoir: production performance, pressure management, water management, or recovery efficiency.

7. The method of claim 6, wherein the production performance indicates a comparison of current average productivity compared to peak productivity, thereby identifying what amount of material the petroleum reservoir is currently producing versus what the petroleum reservoir has produced over a past period of time.

8. The method of claim 7, wherein the production performance further takes into account production levels at different petroleum reservoirs within the petroleum producing field, identifying an amount of material recovered at other petroleum reservoirs within the petroleum producing field.

9. The method of claim 6, wherein the pressure management indicates a measurement of current pressure over initial pressure, resulting in a cumulative voidage replacement ratio (VRR) that indicates a ratio of total volume extracted over a specified time frame.

10. The method of claim 6, wherein the water management indicates a change in water cut over a specified time frame, the water cut comprising a ratio of water produced versus oil produced, and an indication of water injection efficiency that measures how much water has been injected versus oil extracted from the petroleum reservoir.

11. The method of claim 6, the recovery efficiency indicates a comparison of expected ultimate recovery (EUR) to a specified benchmark amount, the EUR indicating an approximation of an amount of oil or gas that is potentially recoverable or has already been recovered from the petroleum reservoir.

12. A computer program product comprising one or more computer storage media having thereon computer-executable instructions that, when executed by one or more processors of a computing system, cause the computing system to instantiate a user interface comprising the following:
an interactive production performance indicator configured to illustrate a production performance rating for a petroleum producing field, the production performance rating being based on data captured at the petroleum producing field by one or more hardware-based sensors;
an interactive pressure management indicator configured to illustrate a pressure management rating for the petroleum producing field, the pressure management rating indicating a ratio of current pressure to initial pressure in the petroleum producing field;
an interactive water management indicator configured to illustrate a water management rating for the petroleum producing field, the water management rating indicating a change in water cut over a specified time;
an interactive gas management indicator configured to illustrate a gas management rating for the petroleum producing field, the gas management rating indicating a ratio of production gas-to-oil ratio (GOR) to solution GOR;
an interactive recovery efficiency indicator configured to illustrate a recovery efficiency rating for the petroleum producing field, the recovery efficiency rating indicating a ratio of an estimated ultimate recover (EUR) to a specified EUR benchmark;
a summary indicator providing an overall score for reservoir management competency at the petroleum producing field, the summary indicator comprising a combination of scores from the production performance, pressure management, water management, gas management and recovery efficiency indicators; and
at least one control element that allows control over operation of one or more production units at the petroleum producing field according to the summary indicator.

13. The computer program product of claim 12, wherein the control element of the user interface controls automatically providing operational commands to one or more of the production units.

14. The computer program product of claim 13, wherein the control element causes different operational commands to be sent to the production units based on the overall score of the summary indicator.

15. The computer program product of claim 12, wherein the user interface allows users to interact with each indicator to view a representation of underlying calculations for that indicator.

16. The computer program product of claim 12, wherein the user interface includes color and design schemes that allow a user to view and understand the summary indicator and combination of scores.

17. A computer system comprising the following:
one or more processors;
system memory;
a measuring component configured to measure, using one or more hardware-based sensors positioned in a petroleum reservoir supplying the petroleum producing field, physical or geological characteristics of the petroleum reservoir;
a reservoir management competency scoring system that evaluates a specific set of objective criteria that reflect a level of reservoir management competency at the petroleum producing field, wherein the reservoir management competency scoring system includes a gas management rating that indicates a ratio of production gas-to-oil ratio (GOR) to solution GOR;
a rating generator configured to automatically generate, according to the objective set of criteria of the reservoir management competency scoring system, a reservoir management rating for the petroleum reservoir based at least in part on data measured by the one or more sensors placed in the petroleum reservoir; and
an operations control unit that controls operation of one or more production units, based on the generated reservoir management rating, to direct extraction operations at the petroleum producing field.

18. The computer system of claim 17, further comprising generating an interactive scorecard based on the reservoir management rating, such that the interactive scorecard indicates how effective a company's reservoir management is, and allows users to drill down into underlying causes for the rating.

19. The computer system of claim 18, further comprising generating at least a partial company valuation based on the scorecard indication of how well the reservoir is being managed.

* * * * *